(12) United States Patent
Osadchy

(10) Patent No.: US 7,848,787 B2
(45) Date of Patent: Dec. 7, 2010

(54) RELATIVE IMPEDANCE MEASUREMENT

(75) Inventor: Daniel Osadchy, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 1114 days.

(21) Appl. No.: 11/177,861

(22) Filed: Jul. 8, 2005

(65) Prior Publication Data

US 2007/0038078 A1 Feb. 15, 2007

(51) Int. Cl.
- A61B 5/04 (2006.01)
- A61B 5/05 (2006.01)
- A61B 5/06 (2006.01)
- A61B 19/00 (2006.01)

(52) U.S. Cl. .................. 600/373; 600/547; 600/550; 128/899

(58) Field of Classification Search ............ 600/424, 600/547, 372, 373, 546, 550; 128/899
See application file for complete search history.

(56) References Cited

U.S. PATENT DOCUMENTS

| | | | |
|---|---|---|---|
| 4,642,570 A | 2/1987 | Sternberg | |
| 5,341,807 A | 8/1994 | Nardella | |
| 5,365,461 A | 11/1994 | Stein | |
| 5,447,529 A | 9/1995 | Marchlinski et al. | |
| 5,697,377 A * | 12/1997 | Wittkampf | 600/374 |
| 5,836,990 A | 11/1998 | Li | |
| 5,899,860 A | 5/1999 | Pfeiffer et al. | |
| 5,935,079 A | 8/1999 | Swanson et al. | |
| 5,944,022 A | 8/1999 | Nardella et al. | |
| 5,983,126 A | 11/1999 | Wittkampf | |
| 6,050,267 A * | 4/2000 | Nardella et al. | 128/899 |
| 6,095,150 A | 8/2000 | Panescu et al. | |
| 6,456,864 B1 | 9/2002 | Swanson et al. | |
| 6,471,693 B1 | 10/2002 | Carroll et al. | |
| 6,546,270 B1 * | 4/2003 | Goldin et al. | 600/374 |
| 6,569,160 B1 | 5/2003 | Goldin et al. | |
| 2002/0046756 A1 | 4/2002 | Laizzo | |
| 2003/0045871 A1 | 3/2003 | Jain et al. | |
| 2007/0038078 A1 * | 2/2007 | Osadchy | 600/424 |

FOREIGN PATENT DOCUMENTS

WO        WO 98/48722 A1        11/1998

OTHER PUBLICATIONS

Operating Instructions General Devices Model EIM 105-30Hz Prep-Check Electrode Impedance Meter; Manual, Apr. 22, 2004, pp. 1-5, Ridgefield, New Jersey.
EPO Search Report 06253573.7-1265 dated Apr. 3, 2007.
Biosense Webster, Inc., U.S. Appl. No. 11/030,934, pending.
EPO Search Report 06253573 dated Jun. 26, 2007.
EPO Search Report 08075590 dated Aug. 27, 2008.

* cited by examiner

Primary Examiner—Max Hindenburg
Assistant Examiner—Sean P Dougherty
(74) Attorney, Agent, or Firm—Louis J. Capezzuto

(57) ABSTRACT

A method for calibrating impedance includes coupling at least first, second, and third electrodes at respective locations to a surface of a body of a subject. A first current passing through the body between the first and second body-surface electrodes is measured, and a second current passing through the body between the first and third body-surface electrodes is measured. From the first and second currents, a contact factor is derived that is indicative of the impedance between at least one of the body-surface electrodes and the surface of the body. Also described are methods for sensing the position of a probe and for detecting tissue contact based on a relation between currents from the probe to body-surface electrodes.

6 Claims, 3 Drawing Sheets

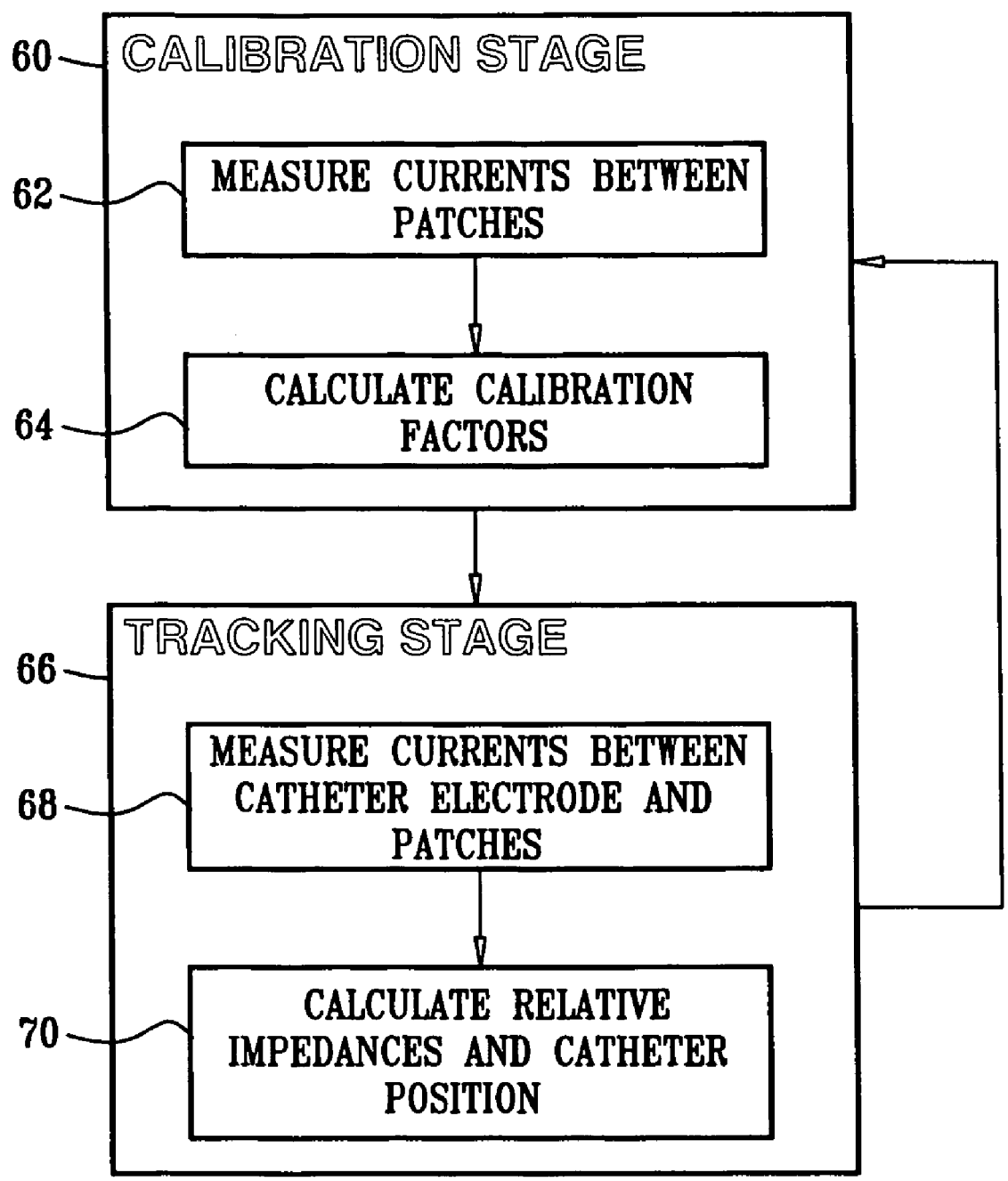

RELATIVE IMPEDANCE MEASUREMENT

CROSS-REFERENCE TO RELATED APPLICATIONS

This application is related to U.S. patent application Ser. No. 11/030,934, filed Jan. 7, 2005, which is assigned to the assignee of the present patent application and whose disclosure is incorporated herein by reference.

FIELD OF THE INVENTION

The present invention relates generally to tracking movement of an object placed within a living body, and specifically to object tracking using impedance measurements.

BACKGROUND OF THE INVENTION

Many medical procedures involve introducing an object into a patient's body and sensing the object's movement. To support these procedures, various position sensing systems have been developed or envisioned in the prior art.

For example, U.S. Pat. Nos. 5,697,377 and 5,983,126 to Wittkampf, whose disclosures are incorporated herein by reference, describe a system in which three substantially orthogonal alternating signals are applied through the patient. A catheter is equipped with a measuring electrode, which for cardiac procedures is positioned at various locations either against the patient's heart wall or within a coronary vein or artery. A voltage is sensed between the catheter tip and a reference electrode, preferably a surface electrode on the patient. Three processing channels are used to separate out the three components as x, y and z signals, from which calculations are made for determination of the three-dimensional location of the catheter tip within the body.

U.S. Pat. No. 5,944,022 to Nardella, whose disclosure is incorporated herein by reference, describes a similar system for detecting the position of a catheter. The system includes three sets of excitation electrodes, with one set disposed in each of three intersecting axes. A signal processor measures a voltage indicative of impedance between a detection electrode disposed on the catheter and each of the three sets of excitation signals in order to determine the X coordinate, Y coordinate and Z coordinate of the catheter.

Additional methods for detecting impedance along axes between excitation electrodes are disclosed by U.S. Pat. No. 5,899,860 to Pfeiffer; U.S. Pat. No. 6,095,150 to Panescu; U.S. Pat. No. 6,456,864 to Swanson; and U.S. Pat. No. 6,050,267 to Nardella, all of whose disclosures are incorporated herein by reference.

Impedance measurements are also used in assessing contact between an electrode and tissue inside the body. For example, methods for determining contact between a catheter electrode and internal tissue, based on the impedance between the catheter electrode and a return electrode, are described in U.S. Pat. No. 5,935,079 to Swanson, et al., U.S. Pat. No. 5,836,990 to Li, U.S. Pat. No. 5,447,529 to Marchlinski, et al., and U.S. Pat. No. 6,569,160 to Goldin, et al., all of whose disclosures are incorporated herein by reference. U.S. Pat. No. 5,341,807 to Nardella, whose disclosure is incorporated herein by reference, describes a system for detecting when an ablation electrode contacts endocardium tissue, utilizing separate circuits for position monitoring and for tissue contact monitoring. When the ablation electrode touches internal tissue, the impedance from the body-surface to the electrode increases because less of the electrode is in contact with the electrolytic fluid (i.e., blood) that generally surrounds the probe.

SUMMARY OF THE INVENTION

Embodiments of the present invention provide efficient apparatus and methods for calibrating and for stabilizing impedance-based systems used for tracking an intrabody object.

The above-mentioned U.S. patent application Ser. No. 11/030,934 describes a position tracking system in which impedance measurements between an intrabody probe and the surface of a patient's body are used to track the probe position. These measurements involve passing a current between an electrode fixed to the probe and several electrodes on the body-surface. Such measurements are sensitive to variations in the electrical contact of the body-surface electrodes, as well as to variations in the extent of contact between the probe electrode and internal tissue.

Body-surface electrode contact may fluctuate due to factors such as sweat and partial electrode lifting. Movement of the probe may bring the probe electrode into contact with internal tissue, thereby causing sudden changes in the impedance measured from the body-surface to the probe electrode. Both factors of surface electrode contact and internal tissue contact may affect the stability of position measurements.

In some embodiments of the present invention, the quality of the body-surface electrode contact is calibrated periodically to correct for contact fluctuations. In the disclosed embodiments, calibration is performed by measuring the current between pairs of body-surface electrodes. These currents are indicative of the total impedance of the current path through the body between the electrodes, including the electrode contact impedance. Techniques described hereinbelow are used to extract from the multiple current measurements a calibration factor for body-surface electrode contact of each electrode. The process is typically repeated at regular intervals in order to maintain accurate calibration.

Further embodiments of the present invention provide means and methods for correcting impedance variations due to internal tissue contact. To achieve this correction, the probe electrode is tracked by a relative, rather than absolute, measure of impedance. Relative impedance is measured by comparing the impedance from the probe electrode to one body-surface electrode with the sum of several impedances measured between the probe electrode and several respective body-surface electrodes. When the impedances measured to the several body-surface electrodes change by the same relative amount, the change is attributed to internal tissue contact and the change is factored out of the location calculation.

There is therefore provided, in accordance with an embodiment of the present invention, a method for calibrating impedance, including:

coupling at least first, second, and third electrodes at respective locations to a surface of a body of a subject;

measuring a first current passing through the body between the first and second body-surface electrodes;

measuring a second current passing through the body between the first and third body-surface electrodes; and deriving a contact factor indicative of the impedance between at least one of the body-surface electrodes and the surface of the body using the first and second currents.

Typically, deriving the contact factor includes determining a value of relative impedance using a relation between the first current and a sum of the first and second currents. In some embodiments, deriving the contact factor includes determining three or more values of the relative impedance and solving a set of linear equations whose parameters include the three or more values and distances between the body-surface electrodes.

In further embodiments, the method includes:

inserting a probe including a fourth electrode into the body;

measuring a third current through the body between the fourth electrode and at least one of the body-surface electrodes; and sensing a position of the probe responsively both to the contact factor of the at least one body-surface electrode and to the third current.

In some embodiments, sensing the position includes determining a relative distance between the probe and the at least one body-surface electrode.

Typically, at least one of the first, second, and third body-surface electrodes includes an adhesive conductive patch.

There is further provided a method for position sensing, including:

inserting a probe including a probe electrode into a body of a subject;

measuring a first current passing through the body between the probe electrode and a first body-surface electrode coupled to a surface of the body;

measuring a second current passing through the body between the probe electrode and a second body-surface electrode coupled to the surface of the body;

calculating a relation between the first and second currents; and tracking movement of the probe within the body responsively to the relation.

Typically, calculating the relation includes determining a value of relative impedance between the probe electrode and each of the body-surface electrodes. In some embodiments, determining the value of relative impedance includes finding a quotient of the first current and the sum of the first and second currents. In disclosed embodiments, calculating the relation includes determining at least two values of relative impedance between the probe electrode and the first and second body-surface electrodes and solving a set of linear equations whose parameters include the at least two values. In further embodiments, tracking the movement of the probe includes determining that a change in the first and second currents that does not significantly change the relation between the first and second currents is indicative of contact of the probe electrode with tissues of varying impedance within the body, and not due to the movement of the probe. In still further embodiments, the relation between the first and second currents is indicative of a relative impedance between the probe and the first and second body-surface electrodes.

There is also provided, in accordance with an embodiment of the present invention, a method for detecting tissue contact, including:

inserting a probe including a probe electrode into a body of a subject, such that the probe electrode makes contact with a tissue inside the body;

measuring a first current passing through the body between the probe electrode and a first body-surface electrode coupled to a surface of the body;

measuring a second current passing through the body between the probe electrode and a second body-surface electrode coupled to the surface of the body;

calculating a relation between the first and second currents; and detecting, responsively to the relation, contact between the probe and the tissue.

Typically, detecting the contact between the probe and the tissue includes measuring a change in the first and second currents that does not change the relation between the first and second currents. In some embodiments, the method for detecting tissue contact includes tracking a position of the probe in the body responsively to the first and second currents and correcting the position responsively to detecting the contact between the probe and the tissue.

There is also provided, in accordance with an embodiment of the present invention, apparatus for calibrating impedance, including:

at least first, second and third electrodes adapted to be coupled at respective locations to a surface of a body of a subject; and a control unit, adapted to measure a first current passing through the body between the first and second body-surface electrodes, to measure a second current passing through the body between the first and third body-surface electrodes, and to derive a contact factor indicative of the impedance between at least one of the body-surface electrodes and the surface of the body using the first and second currents.

Typically, the control unit is adapted to derive the contact factor by determining a value of relative impedance, using a relation between the first current and a sum of the first and second currents.

In some embodiments, the control unit is adapted to determine three or more values of the relative impedance and to derive a contact factor by solving a set of linear equations whose parameters include the three or more values and distances between the body-surface electrodes.

In further embodiments, the apparatus includes a probe that includes a fourth electrode and which is adapted to be inserted into the body. The control unit is further adapted to measure a third current through the body between the fourth electrode and at least one of the body-surface electrodes, and to sense a position of the probe responsively both to the contact factor of the at least one of the body-surface electrodes and to the third current.

In some embodiments, the control unit is adapted to sense the position by determining a relative distance between the probe and the at least one body-surface electrode.

There is also provided, in accordance with an embodiment of the present invention, apparatus for position sensing, including:

a probe including a probe electrode and adapted to be inserted into a body of a subject;

first and second body-surface electrodes adapted to be coupled at respective locations to a surface of a body of a subject; and a control unit, adapted to measure a first current passing through the body between the probe electrode and the first body-surface electrode, to measure a second current passing through the body between the probe electrode and the second body-surface electrode, to calculate a relation between the first and second currents, and to track movement of the probe within the body responsively to the relation.

Typically, the control unit is adapted to track movement of the probe by determining a value of relative impedance between the probe electrode and each of the body-surface electrodes.

In disclosed embodiments, the control unit is adapted to determine the value of relative impedance by calculating a quotient of the first current and the sum of the first and second currents.

In some embodiments, the control unit is adapted to derive at least two values of relative impedance and to track movement of the probe by solving a set of linear equations whose parameters include the values of the relative impedance.

In further embodiments, the control unit is adapted to determine that a change in the first and second currents that does not significantly change the relation between the first and second currents is indicative of contact of the probe electrode with tissues of varying impedance within the body, and not due to the movement of the probe. Typically, the relation between the first and second currents is indicative of a relative impedance between the probe and the first and second body-surface electrodes.

There is also provided, in accordance with an embodiment of the present invention, apparatus for detecting tissue contact, including:

a probe including a probe electrode adapted to be inserted into a body of a subject and to make contact with a tissue inside the body;

first and second body-surface electrodes adapted to be coupled at respective locations to a surface of a body of a subject; and a control unit adapted to measure a first current passing through the body between the probe electrode and the first body-surface electrode, to measure a second current passing through the body between the probe electrode and a second body-surface electrode, to calculate a relation between the first and second currents, and to detect, responsively to the relation, contact between the probe and the tissue.

In some embodiments, the control unit is adapted to detect the contact between the probe and the tissue by sensing a change in the first and second currents while sensing no change in the relation between the first and second currents.

Additionally or alternatively, the control unit is adapted to track a position of the probe in the body responsively to the first and second currents and to correct the position responsively to detecting the contact between the probe and the tissue.

The present invention will be more fully understood from the following detailed description of the embodiments thereof, taken together with the drawings in which:

BRIEF DESCRIPTION OF THE DRAWINGS

FIG. 3 is a flow diagram schematically illustrating the processes of calibrating conductance of body-surface electrodes and of tracking catheter movement, in accordance with an embodiment of the present invention.

DETAILED DESCRIPTION OF EMBODIMENTS

Figure 1:
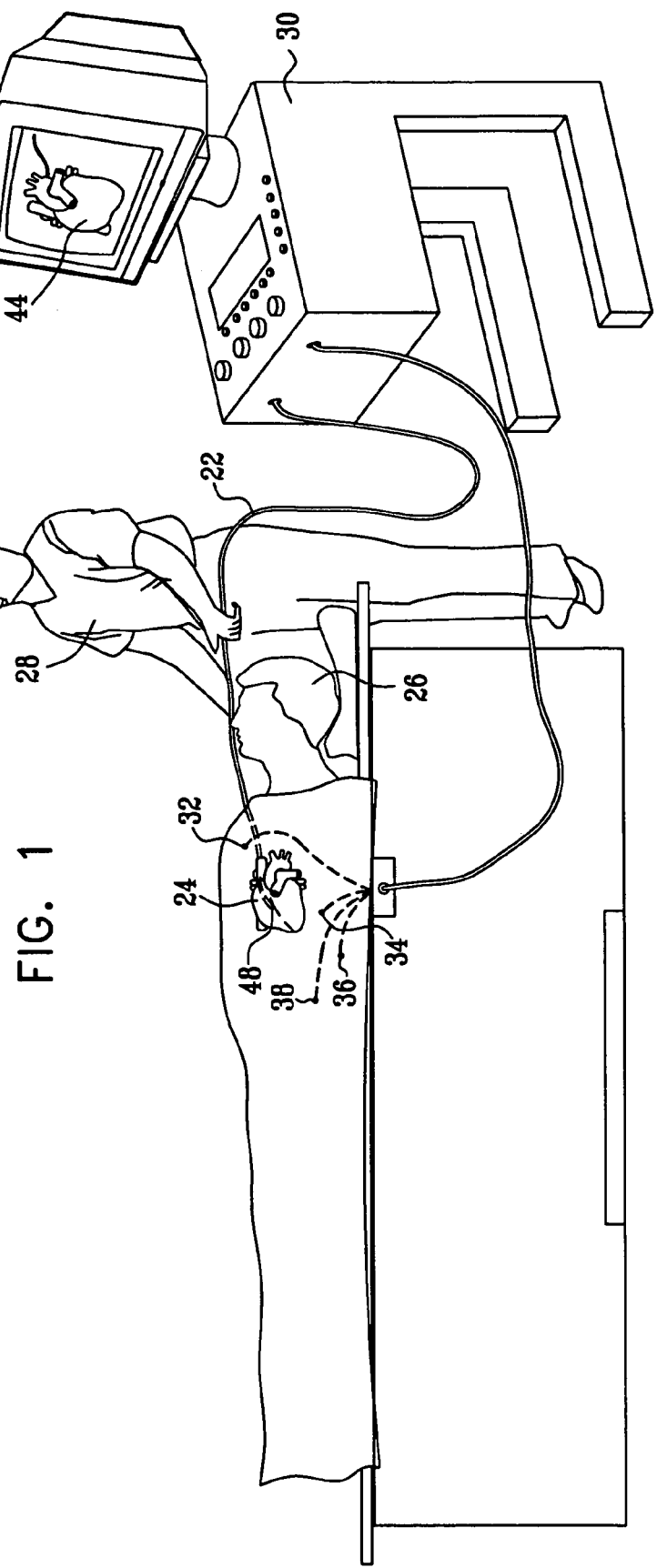
FIG. 1 is a schematic, pictorial illustration of a position tracking system, in accordance with an embodiment of the present invention.

FIG. 1 is a schematic, pictorial illustration of a position tracking system 20, in accordance with an embodiment of the present invention. As described in the above-mentioned U.S. patent application Ser. No. 11/030,934, impedance-based position tracking in system 20 is performed by inserting a probe, such as a catheter 22, into an internal body cavity, such as a chamber of a heart 24 of a subject 26. Typically, the catheter is used for diagnostic or therapeutic treatment performed by medical practitioner 28, such as mapping electrical potentials in the heart or performing ablation of heart tissue. The catheter or other intrabody device may alternatively be used for other purposes, by itself or in conjunction with other treatment devices.

The distal tip of catheter 22 comprises at least one electrode 48. Electrode 48 may be of any suitable shape and size, and may be used for other purposes, as well, such as for electro-physiological sensing or ablation. The electrode is connected by a wire to driver and measurement circuitry in a control unit 30.

A plurality of body-surface electrodes, such as adhesive skin patches 32, 34, 36, and 38 (collectively referred to hereinbelow as patches 32-38) are coupled to a body-surface (e.g., the skin) of subject 26. Patches 32-38 may be placed at any convenient locations on the body-surface in the vicinity of the medical procedure. Typically, the locations of the skin patches are spaced apart. For example, for cardiac applications, patches 32-38 are typically placed around the chest of subject 26.

Patches 32-38 are also connected by wires to control unit 30. The control unit determines position coordinates of catheter 22 inside heart 24 based on the currents measured between the catheter and each of patches 32-38 as described hereinbelow. The control unit drives a monitor 42, which shows the catheter position inside the body. The catheter may be used in generating a map 44 of the heart, and the displayed catheter position may be superimposed on this map or on another image of the heart.

Figure 2:
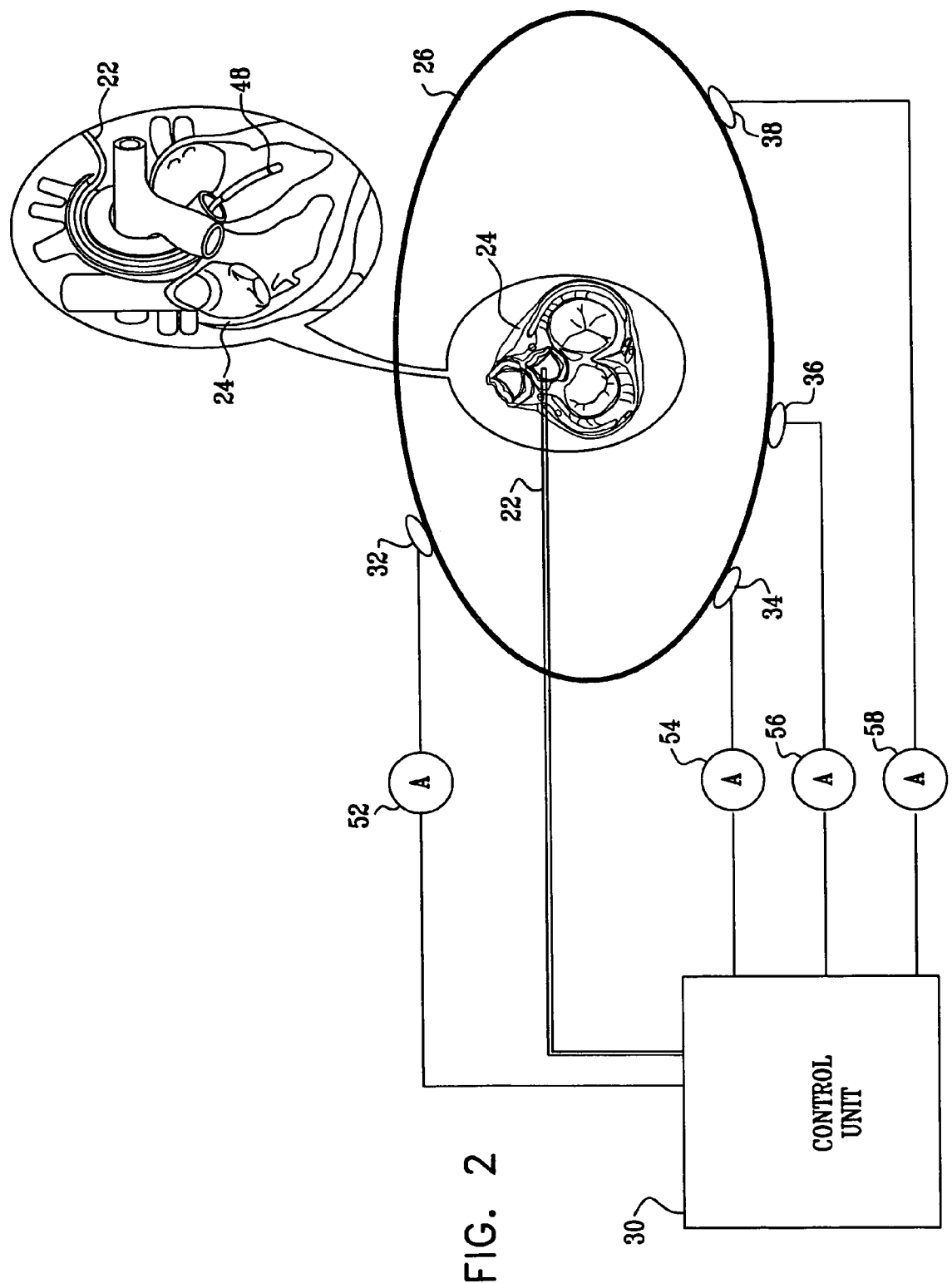
FIG. 2 is a schematic detail view showing interaction between electrodes on a catheter and on the body-surface, in accordance with an embodiment of the present invention.

FIG. 2 is a schematic detail view, showing catheter 22 inside heart 24, in accordance with an embodiment of the present invention. Typically, catheter 22 comprises at least one electrode 48, as described hereinabove. In the pictured embodiment, electrode 48 communicates with one or more of patches 32-38. Control unit 30 drives a current between electrode 48 and one or more of patches 32-38. Currents through the one or more patches (referred to hereinbelow as patch currents) are measured by one or more of respective current measurement circuits 52, 54, 56, and 58 (collectively referred to hereinbelow as circuits 52-58). A measurement circuit is typically configured to be affixed to a body surface patch, or, alternatively, to be situated within control unit 30.

Currents measured by circuits 52-58 are indicative of impedances between the catheter and the respective patches. Using methods described below with reference to FIG. 3, the measured currents may be used to calculate parameters of relative impedance, which are in turn used to derive coordinates of the catheter.

FIG. 3 is a flow diagram schematically illustrating a method for tracking catheter 22 inside heart 24, in accordance with an embodiment of the present invention. The method comprises a patch calibration stage 60 and a tracking stage 66. Patch calibration is typically carried out initially, before practitioner 28 begins manipulating the catheter in the patient's body. Calibration factors derived during calibration stage 60 may be used to correct position measurements made during tracking stage 66. The same configuration of control Unit and electrodes may be used both for calibration stage 60 and for tracking stage 66.

At a measurement step 62 of calibration stage 60, control unit 30 successively drives currents between patches 32-38 and acquires current measurements from respective measurement circuits. For example, a calibration driving current may first be applied to patch 32. The other patches 34, 36, and 38 act as current sinks, such that the driving current from patch 32 is split into three calibration patch currents flowing through patches 34, 36, and 38. The three calibration patch currents are measured using current measurement circuits 54, 56, and 58, respectively. Subsequently, the process is repeated by driving currents from each of patches 34, 36, and 38 in turn, and measuring the patch currents at the other patches.

At a calculation step 64 of calibration stage 60, the currents measured at measurement step 62 are used to derive calibration factors that may be used subsequently during tracking stage 66. In general, for a parallel circuit comprising a set of N patches, when a current I is driven from a patch j to the other N−1 patches in the set, the current measured at a patch i may be represented as $I_{ij}$, and is related to the calibration driving current I by the equation:

$$I_{ij} = I \frac{\sigma_{ij}}{\sum_{\substack{k=1,\\k\neq j}}^{N} \sigma_{kj}} \quad (1)$$

wherein $\sigma_{ij}$ is the conductance between pairs of patches i and j, and the denominator of equation (1) represents the conductance of the complete parallel circuit, which is the sum of the conductances between patch j and each of the other N−1 patches in the set. The calibration patch current $I_{ij}$ may also be written in terms of $R_{ij}$, the impedance between pairs of patches i and j, as follows:

$$I_{ij} = I \frac{1/R_{ij}}{\sum_{\substack{k=1,\\k\neq j}}^{N} 1/R_{kj}} \quad (2)$$

For N patches, there are N(N−1) ordered patch pairs (i, j) for which values of $I_{ij}$ may be measured.

The impedance $R_{ij}$ is approximately modeled as $$R_{ij} = G \cdot C_i \cdot C_j \cdot d_{ij} \quad (3)$$

wherein $C_i$ is a contact factor for patch i, $C_j$ is a contact factor for patch j, $d_{ij}$ is the distance between patches i and j, and G is a general constant representing medium resistivity.

The values for distances, $d_{ij}$, may be determined using position sensing or manual measurement methods. The contact factors, $C_i$ which are indicative of the impedance between the skin and the patch, represent the effect of several phenomena, including patch surface area, skin properties, such as moisture and salinity, and impedance effects related to non-ideal current measurement circuits 52-58. Relative values of $C_i$, that is, values that express each contact factor relative to the sum of all the contact factors, may be solved in terms of the currents, $I_{ij}$, and the distances, $d_{ij}$. The values of $C_i$ subsequently serve as calibration factors for tracking stage 66.

One method for solving for the relative values of $C_i$ consists of substituting equation (3) into equation (2), giving the following set of N(N−1) simultaneous equations:

$$I_{ij} = \frac{I}{GC_iC_jd_{ij}\sum_{\substack{k=1,\\k\neq j}}^{N}\frac{1}{GC_kC_jd_{kj}}} = \frac{I}{C_id_{ij}\sum_{\substack{k=1,\\k\neq j}}^{N}\frac{1}{C_kd_{kj}}}.$$

Calculation of the values of $C_i$ may be simplified by calculating an intermediate value, $\hat{R}_{ij}$, representing the relative impedance between patch j and patch i. For a given driving current I between patch j and the other N−1 patches, $\hat{R}_{ij}$ is defined as the impedance between patch j and patch i, divided by the sum of the impedances between patch j and each of the other N−1 patches. That is, $\hat{R}_{ij}$ is defined as follows:

$$\hat{R}_{ij} \equiv \frac{R_{ij}}{\sum_{\substack{k=1,\\k\neq j}}^{N} R_{kj}} \quad (4)$$

Substituting equation (3) into equation (4), gives the following set of N(N−1) simultaneous equations:

$$\hat{R}_{ij} = \frac{G \cdot C_i \cdot C_j \cdot d_{ij}}{\sum_{\substack{k=1,\\k\neq j}}^{N} G \cdot C_k \cdot C_j \cdot d_{kj}} = \frac{C_i d_{ij}}{\sum_{\substack{k=1,\\k\neq j}}^{N} C_k d_{kj}}. \quad (5)$$

As is shown in the Appendix, $\hat{R}_{ij}$, can be calculated in terms of the patch currents measured for a given driving current, as follows:

$$\hat{R}_{ij} = \frac{\frac{1}{I_{ij}}}{\sum_{\substack{k=1,\\k\neq j}}^{N} \frac{1}{I_{kj}}}.$$

Thus, in the set of equations (5), the values of $\hat{R}_{ij}$ are known, and the distances $d_{ij}$ are known, and we can therefore derive the remaining unknown values, $C_i$. Rearranging equations (5) gives the following linear system of equations:

$$\hat{R}_{ij}\sum_{\substack{k=1,\\k\neq j}}^{N} C_k d_{kj} - C_i d_{ij} = 0.$$

As $d_{ii}=0$ for all i, the k≠j parameter of the summation is not required. The final linear system of equations may thus be written as:

$$\hat{R}_{ij}\sum_{k=1}^{N} X_k d_{kj} - X_i d_{ij} = 0 \quad (6)$$

wherein $X_i \equiv C_i$ are the patch calibration factors.

The system of equations (6) may be used at calculation step 64 to find the relative values of $X_i$. The system of equations is of the type $A \cdot X = 0$ wherein A is an N(N−1)×N matrix that depends on $\hat{R}_{ij}$ and $d_{ij}$, and wherein X is a vector representing the N values of $X_i$. Singular value decomposition (SVD) analysis of A or eigenvector analysis of the N×N matrix $A^T A$ provides a solution for X, as is known in the art.

The relative values of $X_i$ are subsequently used during tracking stage 66 to prevent fluctuations in body-surface electrode contact from affecting the position measurements.

During the tracking stage, the control unit drives currents from electrodes 48 to the patches. Typically, at certain intervals during the procedure, tracking stage 66 is interrupted, and calibration stage 60 is repeated.

Tracking stage 66 begins with a measurement step 68, at which control unit 30 drives a current between catheter electrode 48 and two or more of patches 32-38 and measures the currents at each patch, according to the method described above in FIG. 2.

In an embodiment of the present invention, after the currents between catheter electrode 48 and respective patches 32-38 are measured at step 68, relative impedances between the catheter electrode and the patches are calculated at a position calculation step 70, in a manner similar to that used to determine relative impedances between patches at step 64. The relative impedances between the catheter electrode and the patches provide an indication of the position of the catheter, which control unit 30 may then display on monitor 42, as shown in FIG. 1.

At step 70, the control unit typically applies the patch calibration factors derived during calibration stage 60, although tracking stage 66 may also be carried out without patch calibration. The impedances measured between the catheter electrode and patches 32-38 are used (along with the patch calibration factors) to calculate relative distances between the catheter electrode and each of the patches. These distances may then be used to determine absolute spatial coordinates of the catheter. Relative distances are determined using the equations derived hereinbelow.

The impedance between the catheter electrode and a patch i may be modeled as $$R_i = G \cdot X_i C_{cath} \cdot d_i \tag{7}$$

wherein $X_i$ is the calibration factor for patch i, $C_{cath}$ is a contact constant for catheter electrode 48, $d_i$ is the distance between patch i and catheter electrode 48, and G is the general constant representing medium resistivity. The current driven from the catheter electrode and flowing into a patch i is represented as patch current $I_i$ and is related to the driving current I by the equation:

$$I_i = I \frac{1/R_i}{\sum_{k=1}^{N} 1/R_k}.$$

Following a derivation similar to that described above at step 64, relative values of distance $d_i$ may be determined by generating a set of equations for relative impedances, $\hat{R}_i$, which is defined as:

$$\hat{R}_i \equiv \frac{R_i}{\sum_{k=1}^{N} R_k}. \tag{8}$$

Substituting equation (7) into equation (8), gives the following set of N simultaneous equations:

$$\hat{R}_i = \frac{G \cdot X_i \cdot C_{cath} \cdot d_i}{\sum_{k=1}^{N} G \cdot X_k \cdot C_{cath} \cdot d_k} = \frac{X_i d_i}{\sum_{k=1}^{N} X_k d_k}. \tag{9}$$

$\hat{R}_i$ is independent of both the medium resistivity G and the catheter contact $C_{cath}$; i.e., position measurements made in this fashion are insensitive to impedance variations caused by catheter contact with internal body tissues. Following a derivation similar to that described in the Appendix, $\hat{R}_i$ can be calculated in terms of the patch currents measured for a given driving current, as follows:

$$\hat{R}_i = \frac{\frac{1}{I_i}}{\sum_{k=1}^{N} \frac{1}{I_k}}.$$

The only unknown variables in the set of equations (9) are therefore the relative values of $d_i$. Rearranging equations (9) gives the following linear system of equations:

$$\hat{R}_i \sum_{k=1}^{N} X_k d_k - X_i d_i = 0. \tag{10}$$

The system of equations (10) has N unknowns $d_i$ and N equations and is of the type A·d=0 wherein A is an N×N matrix that depends on $\hat{R}_i$ and $X_i$. The solutions for the N relative values of $d_i$ are found by SVD analysis of A or eigenvector analysis of $A^T A$.

If an initial catheter position is known, the relative distance values $d_i$ may be used at calculation step 70 to derive the relative movement of the catheter from the initial catheter position.

Alternatively or additionally, when four or more patches are used, absolute coordinates of the catheter electrode may be calculated at calculation step 70. Four unknown parameters are derived, including the three spatial coordinates of the catheter electrode, which may be represented as a vector $\vec{q}$, and a multiplicative constant, $\alpha$, which generates the absolute distances from the relative distances, $d_i$, calculated above.

To solve for the four parameters, the absolute distance between the catheter electrode and patch i, represented as a $\alpha \cdot d_i$, is equated to the absolute difference between the spatial coordinates of the catheter electrode and of the patch i, which may be represented as $\|\vec{q} - \vec{p}_i\|$, wherein $\vec{p}_i$ is a vector representing the coordinates of patch i. The equality provides a set of N equations of the form:

$$\|\vec{q} - \vec{p}_i\| = \alpha \cdot d_i. \tag{11}$$

The values for $\vec{q}$ and $\alpha$ in the set of equations (11) may be solved using a minimization algorithm, such as the least squares method, which may be performed by minimization of the expression:

$$\sum_{i=1}^{N} (\|\vec{q} - \vec{p}_i\| - \alpha \cdot d_i)^2. \tag{12}$$

In an alternative embodiment of the invention, the relative impedance, defined above as a ratio of an impedance and the sum of impedances, may be defined as a difference between measured impedances. In another alternative embodiment, a ratio may be taken between an impedance reading at each body-surface patch and the sum of readings at several other patches.

When catheter 22 moves, the relative impedance with respect to at least one patch changes. The measurement of the change in relative impedance thereby permits tracking of the catheter.

By contrast, when catheter electrode 48 touches internal tissue, the patch currents will change, but the values of relative impedance will not change. Consequently, as noted above, errors in position measurement due to tissue contact are reduced when the methods described above are used. These methods further provide a means of evaluating internal tissue contact by sensing when changes in current are not reflected by changes in the relative impedances.

Although the methods described above are illustrated in the context of a catheter-based system for diagnosis or treatment of conditions of the heart, the principles of the present invention may similarly be used in position tracking systems for the diagnosis or treatment of other body structures, such as the brain, spine, skeletal joints, urinary bladder, gastrointestinal tract, prostrate, and uterus.

Furthermore, although the impedance calibration and position tracking techniques of stages 60 and 66 are described hereinabove as two complementary parts of a single position tracking method, in alternative embodiments these techniques may be used independently of one another. For example, the patch calibration technique described above may be used to determine and measure changes in the impedances of electrodes in other impedance-based tracking systems, as well as in other diagnostic and therapeutic techniques that use multiple electrodes on and/or in the body. Furthermore, position tracking based on relative impedance, as in stage 66 above, is a useful method of increasing the accuracy and reliability of position measurements even in the absence of specific calibration of the impedances of body-surface electrodes.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

APPENDIX

Derivation of Relation between Relative Impedance and Patch Currents

In general, for a parallel circuit comprising a set of N nodes, such as electrode patches, wherein a current I is driven from a node j to the other N−1 nodes in the set, the current measured at a node i may be represented as $I_{ij}$, and is related to impedances between the nodes, $R_{ij}$, by the equation:

$$I_{ij} = I \frac{1/R_{ij}}{\sum_{\substack{n=1,\\n\neq j}}^{N} 1/R_{nj}}. \tag{A1}$$

Inverting both sides of the equation (A1) gives an equation for the inverse of $I_{ij}$, as follows:

$$\frac{1}{I_{ij}} = \frac{1}{I} \cdot \frac{\sum_{\substack{n=1,\\n\neq j}}^{N} 1/R_{nj}}{1/R_{ij}} = \frac{1}{I} \cdot R_{ij} \sum_{\substack{n=1,\\n\neq j}}^{N} 1/R_{nj}. \tag{A2}$$

The sum of inverses of all $I_{ij}$ for a given driving current is $$\sum_{\substack{k=1,\\k\neq j}}^{N} 1/I_{kj}.$$

Dividing both sides of (A2) by this sum gives:

$$\frac{\frac{1}{I_{ij}}}{\sum_{\substack{k=1,\\k\neq j}}^{N} 1/I_{kj}} = \frac{\frac{1}{I} \cdot R_{ij} \sum_{\substack{n=1,\\n\neq j}}^{N} 1/R_{nj}}{\sum_{\substack{k=1,\\k\neq j}}^{N} 1/I_{kj}} \tag{A3}$$

$$= \frac{\frac{1}{I} \cdot R_{ij} \sum_{\substack{n=1,\\n\neq j}}^{N} 1/R_{nj}}{\sum_{\substack{k=1,\\k\neq j}}^{N} \left( \frac{1}{I} \cdot R_{kj} \sum_{\substack{n=1,\\n\neq j}}^{N} 1/R_{nj} \right)}$$

$$= \frac{\frac{1}{I} \cdot R_{ij} \sum_{\substack{n=1,\\n\neq j}}^{N} 1/R_{nj}}{\sum_{\substack{k=1,\\k\neq j}}^{N} \left( \frac{1}{I} \cdot R_{kj} \sum_{\substack{n=1,\\n\neq j}}^{N} 1/R_{nj} \right)}$$

$$= \frac{\frac{1}{I} \cdot R_{ij} \sum_{\substack{n=1,\\n\neq j}}^{N} 1/R_{nj}}{\frac{1}{I} \cdot \sum_{\substack{n=1,\\n\neq j}}^{N} 1/R_{nj} \sum_{\substack{k=1,\\k\neq j}}^{N} 1/R_{kj}}$$

$$= \frac{R_{ij}}{\sum_{\substack{k=1,\\k\neq j}}^{N} 1/R_{kj}}$$

As described in the Specification hereinabove, a relative impedance, $\hat{R}_{ij}$, is defined as the impedance between node j and node i, divided by the sum of the impedances between node j and each of the other N−1 nodes. $\hat{R}_{ij}$ can thus be expressed as:

$$\hat{R}_{ij} \equiv \frac{R_{ij}}{\sum_{\substack{k=1,\\k\neq j}}^{N} 1/R_{kj}} \tag{A4}$$

Substituting equation (A3) into equation (A4), gives an equation for $\hat{R}_{ij}$ in terms of $I_{ij}$, as follows:

$$\hat{R}_{ij} = \frac{\frac{1}{I_{ij}}}{\sum_{\substack{k=1,\\k\neq j}}^{N} \frac{1}{I_{kj}}}.$$

The invention claimed is:

1. A method for position sensing, comprising:
   inserting a probe comprising a probe electrode into a body of a subject;
   measuring a first current passing through the body between the probe electrode and a first body-surface electrode coupled to a surface of the body;
   measuring a second current passing through the body between the probe electrode and a second body-surface electrode coupled to the surface of the body;
   calculating a relation between the first and second currents, the relation being indicative of a value of relative impedance between the probe electrode and each of the body-surface electrodes, and being based on a quotient of the first current and a sum of the first and second currents; and
   tracking movement of the probe within the body responsively to the relation.

2. The method according to claim 1, wherein calculating the relation comprises:
   determining at least two values of relative impedance between the probe electrode and the first and second body-surface electrodes, and
   solving a set of linear equations having parameters comprising the at least two values of relative impedance.

3. The method according to claim 1, wherein tracking the movement of the probe comprises determining that a change in the first and second currents that does not change the relation between the first and second currents is indicative of contact of the probe electrode with tissues of varying impedance within the body, and not due to the movement of the probe.

4. Apparatus for position sensing, comprising:
   a probe, comprising a probe electrode, adapted to be inserted into a body of a subject;
   a first body-surface electrode and a second body-surface electrode, each adapted to be coupled at respective locations to a surface of the body; and
   a control unit, adapted to measure a first current passing through the body between the probe electrode and the first body-surface electrode, to measure a second current passing through the body between the probe electrode and the second body-surface electrode, to calculate a relation between the first and second currents, and to track movement of the probe within the body responsively to the relation,
   wherein the relation is indicative of a value of relative impedance between the probe electrode and each of the body-surface electrodes, and is based on a quotient of the first current and a sum of the first and second currents.

5. The apparatus according to claim 4, wherein the control unit is adapted to derive at least two values of relative impedance and to track movement of the probe by solving a set of linear equations having parameters comprising the at least two values of the relative impedance.

6. The apparatus according to claim 4, wherein the control unit is adapted to determine that a change in the first and second currents that does not change the relation between the first and second currents is indicative of contact of the probe electrode with tissues of varying impedance within the body, and not due to the movement of the probe.

* * * * *